Figure 3:
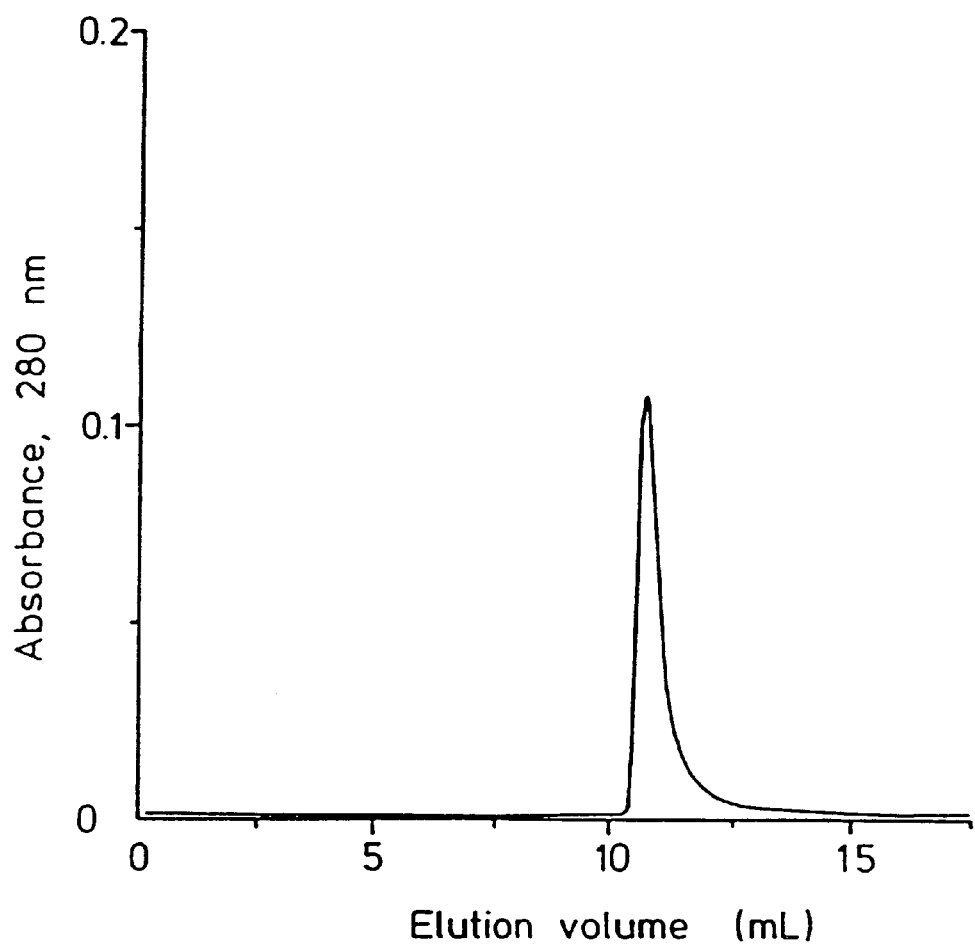

United States Patent [19]
Venge

[11] Patent Number: 6,136,526
[45] Date of Patent: *Oct. 24, 2000

[54] USE OF HUMAN NEUTROPHIL LIPOCALIN (HNL) AS A DIAGNOSTIC MARKER AND ANTI-HNL-ANTIBODY PREPARATION

[76] Inventor: Per Venge, Skolgatan 23, S-753 12 Uppsala, Sweden

[*] Notice: This patent issued on a continued prosecution application filed under 37 CFR 1.53(d), and is subject to the twenty year patent term provisions of 35 U.S.C. 154(a)(2).

[21] Appl. No.: 08/722,054

[22] PCT Filed: Apr. 21, 1995

[86] PCT No.: PCT/SE96/00439

§ 371 Date: Jan. 6, 1997

§ 102(e) Date: Jan. 6, 1997

[87] PCT Pub. No.: WO95/29404

PCT Pub. Date: Nov. 2, 1995

[30] Foreign Application Priority Data

Apr. 21, 1994 [SE] Sweden .................................. 9401351

[51] Int. Cl.$^7$ ............................ C12Q 1/00; G01N 33/53; G01N 33/567; G01N 33/542
[52] U.S. Cl. ................................. 435/4; 435/7.1; 435/7.2; 435/7.24; 435/7.72; 435/7.9; 435/7.92; 436/501; 436/536; 530/387.1; 530/388.1
[58] Field of Search .................................. 435/7.2, 4, 7.1, 435/7.24, 7.72, 7.9, 7.92; 530/387.1, 388.1; 436/501, 536

[56] References Cited

U.S. PATENT DOCUMENTS 4,659,678  4/1987  Forrest et al. .
5,200,319  4/1993  Arnaout et al. .

OTHER PUBLICATIONS

Blood, vol. 83, No. 3, 1994, Lars Kjeldsen et al, "Identification of Neutrophil Gelatinase–Associated Lipocalin as a Novel Matrix Protein of Specific Granules in Human Neutrophils," pp. 799–807, see p. 806, left paragraph.

The Journal of Biological Chemistry, vol. 268, No. 14, May 1993, Lars Kjeldsen et al, "Isolation and Primary Structure of NGAL, a Novel Protein Associated with Human Neutrophil Gelatinase," see p. 10425–10432.

National Library of Medicine (NLM), File Medline, Medline accession No. 94169380, Kjeldsen, L. et al: "Isolation and Characterization of Gelatinase Granules from Human Neutrophils," and Blood 1994, Mar. 15; 83(6):1649–9.

Blood, vol. 82, No. 10, Nov. 1993, Lars Kjeldsen et al, "Structural and Functional Heterogeneity Among Peroxidase–Negative Granules in Human Neutrophils: Identification of a Distinct Gealtinase–Containing Granule Subset by Combined Immunocytochemistry and Subcelluloar. . . " pp. 3183–3191.

Venge et al (J. of Leuk. Bio. Supp 1 1990 p. 28).

Allen et al (Biochimica et Biophysica Acta 991 1989 pp 123–133).

Triebel et al (FEBS letters vol. 314 (3) Dec. 1992 pp 386–388).

Sevier et al (Clinical Chem. vol. 27(11) 1981 pp 1797–1806).

Kouppi et al (Scandinavian J. of Inf. Dis. vol. 25(4) 1993 pp 435–440).

*Primary Examiner*—Albert Navarro
*Attorney, Agent, or Firm*—Dinsmore & Shohl LLP

[57] ABSTRACT

Methods of diagnosing human disease comprise measuring a level of human neutrophil lipocalin (HNL) in a sample from an individual human to be diagnosed. A measured value which is higher than the normal level is an indication that the individual suffers from an inflammation.

8 Claims, 2 Drawing Sheets

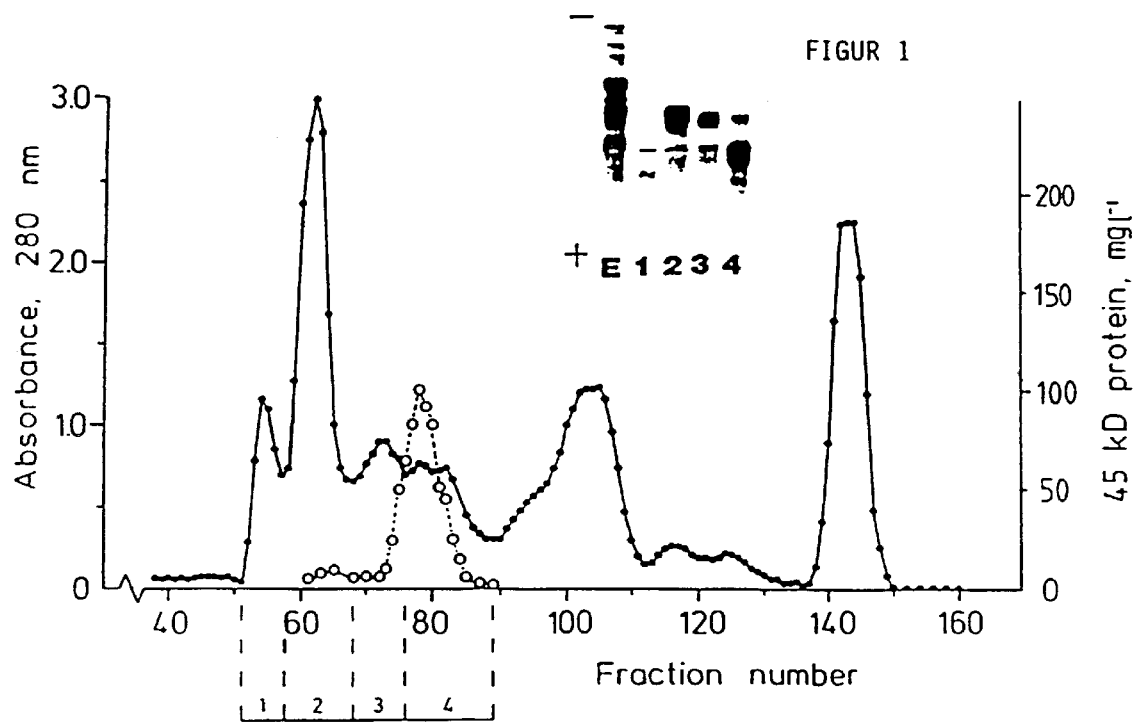
FIGUR 1
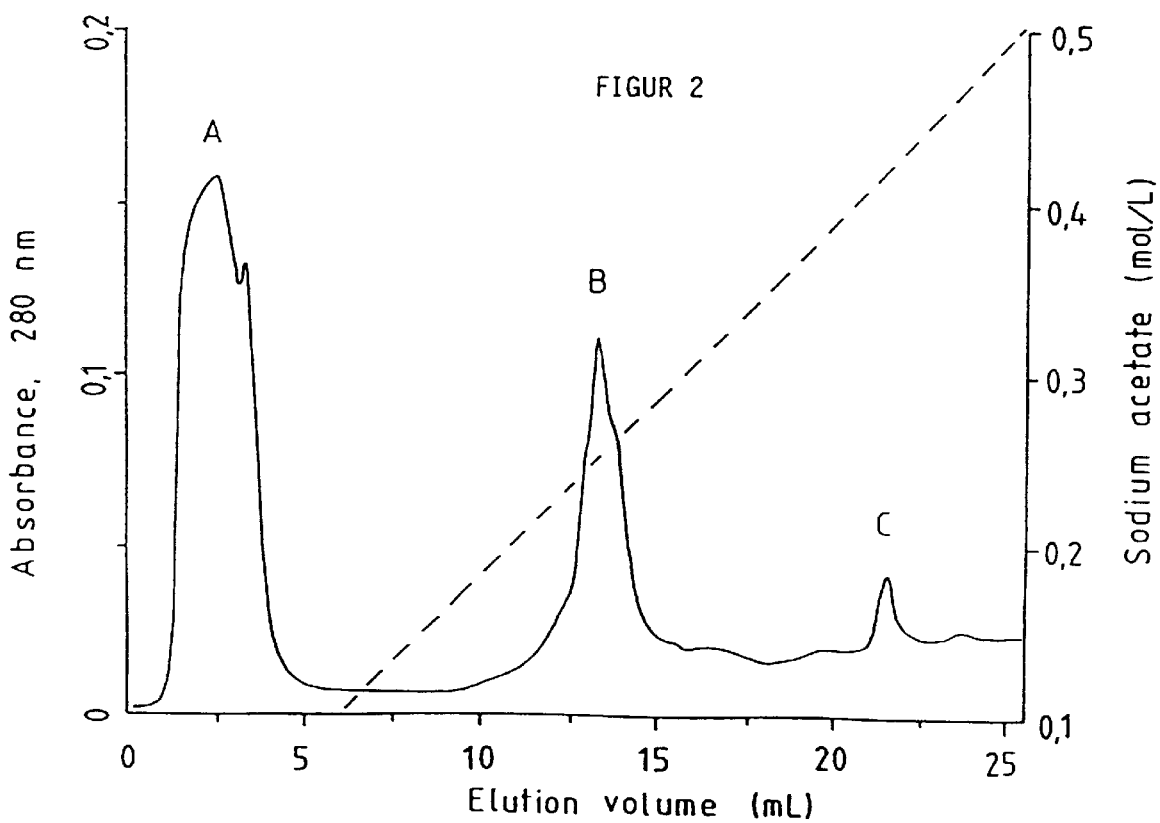
FIGUR 2

USE OF HUMAN NEUTROPHIL LIPOCALIN (HNL) AS A DIAGNOSTIC MARKER AND ANTI-HNL-ANTIBODY PREPARATION

TECHNICAL FIELD AND BACKGROUND

The present invention relates to the use of human neutrophil lipocalin (HNL) as a diagnostic marker, in particular for diagnosis in connection with inflammation that may have a bacterial origin. The determination of the HNL level in a sample from a patient assists in discriminating between bacterial and viral infection.

The main function of human neutrophils is to sense, approach, and destroy invading micro-organisms, in particular pyogenic bacteria. Invading micro-organisms cause degranulation and exocytosis of various granule proteins from neutrophils (Henson, J. Immunol. 107 (1971) 1535–46). The determination of the granule proteins released from neutrophils has long been used as indicators of neutrophil activation in infections and inflammation (Schmekel et al., Inflam. 14 (1990) 447–54; and Lash et al., Blood 61(1983) 885–8). C-reactive protein (CRP) is an acute phase reactant produced in the liver and its measurement has been used in the early diagnosis of bacterial infections.

The results presented herein indicate a sequence identity between HNL and human neutrophil 24 kD N-formyl-peptide binding protein, 25 kD α-2-microglobulin-related protein (Triebel et al., FEBS Lett. 314 (1992) 386-) and neutrophil gelatinase-associated lipocalin (NGAL) (Kjeldsen et al., J. Biol. Chem. 268 (1993) 10425-). The preliminary isolation of HNL has been published (Venge et al., J. Leukocyte Biol. Supplement 1 (1990) 28). During the priority year the complete purification/characterization and assay of human neutrophil lipocalin have been published (Xu et al., Scand. J. Lab. Invest. 54 (1994) 365–76 and Xu et al., J. Immunol. Meth. 171 (1994) 245–52).

OBJECTIVES OF THE INVENTION

There exists a need for new diagnostic markers for bacterial infections and markers that distinguish bacterial infections from viral infections. There also exists a need for markers and methods providing improved specificities for this type of diagnoses.

The present invention provides means that comply with these needs.

THE INVENTION

We have now surprisingly found that HNL derives specifically from neutrophils from which it is released in increased amounts when neutrophils are activated, for instance in connection with inflammation. Inflammatory conditions will be reflected in elevated levels while a lowered neutrophil activity will be reflected in subnormal levels.

In its broadest aspect the invention is thus the use of HNL as a diagnostic marker for neutrophil activity in a liquid sample containing neutrophils.

The method employed comprises the steps:

(i) measuring the level of HNL in an appropriate sample derived from an individual that is to be diagnosed, and then (ii) comparing the level found with the corresponding level (normal level, normal concentration range) for apparently healthy individuals (normal individuals).

If the level found deviates from the normal level this is an indication that the individual suffers from some abnormal condition. A raised level will be indicative of inflammation that mostly is caused by an infection that in turn with high likelihood is of bacterial origin preferably with exclusion of viral infections. A raised level may also be found in samples where the neutrophils have been in contact with exogeneous surfaces so as to release HNL (e.g. plastics or glass surfaces, catheters and extracorporeal arrangements). Subnormal levels may be found in connection with bone marrow transplantation and leukemia or other cases where the number of neutrophils are reduced. It follows that monitoring changes in HNL in samples from a bone marrow transplanted patient will also monitor the success of the transplantation (a progressive increase from subnormal to normal levels will be indicative of the function of the transplant).

It is important to be able to differentiate between bacterial and viral infections in order to determine the correct treatment, for instance during asthmatic exacerbations.

The sample is derived from a human individual and contains neutrophils and/or HNL. Due to the systemic presence of neutrophils potential samples are broncho alveolar lavage fluid, blood (including serum and plasma samples), urine, cerebrospinal fluid and nasal fluid. Blood samples, for instance whole blood, serum and plasma samples, are preferred.

The measurement of HNL can in principle be performed by any method that provides the satisfactory sensitivity, precision, specificity etc. However, as indicated in the experimental section, it is believed that immunoassays are the most preferred methods.

Immunoassays comprise bringing the sample suspected of containing an abnormal level of HNL in contact with an antibody specific for HNL (anti-HNL antibody) in an assay medium under conditions permitting formation of an immune complex comprising HNL and the anti-HNL antibody. The complex formed is thereafter determined by per se known methods to give a quantitative or qualitative measure of the HNL level in the assay medium which in turn is a measure of the HNL level in the sample. In these types of assays the complex as such may be measured or it may be measured by aid of a biospecific affinity reactant labelled with an analytically detectable substance (label), said reactant (and its label) being capable of becoming specifically incorporated into the complex. Examples of suitable biospecific affinity reactants that can be labelled are anti-HNL antibodies, HNL as such, anti-antibodies (anti-anti-HNL antibody) directed against constant regions of an antibody that is present in the complex formed, Proteins A and G etc. Examples of detectable substances (labels) that may be used are luminescers, chromophors, fluorophors, enzymes, enzyme substrates, cofactors, coenzymes etc, radioactive isotopes, particles (metallic or non-metallic), biotin (detected by its reaction with avidin) etc. Some labels change their signal when becoming incorporated into the immune complex while others do not. The former type of labels provides homogeneous immune assays in which there is no need to separate the label incorporated into the complex from the label not incorporated. The latter type of of labels demands the separation to be carried out, for instance by insolubilizing the complex in which the label is or is to be incorporated (heterogeneous assays). In order to achieve an insolubilized complex that contains the label, precipitating agents such as polyethylene glycol and insolubilized and insolubilizable biospecific affinity reactants binding to the complex may be used. Of course this latter type shall not insolubilize the labelled biospecific affinity reactant as such.

The artisan in the field is capable of selecting the appropriate immunoassay protocols, for instance homogeneous or heterogeneous variants, order and type of addition and incubation steps etc. The main point is that the amount of reactants added must be such that the amount of label incorporated into the complex or not incorporated into the complex will reflect the HNL level in the sample.

Normal assay conditions are aqueous media with or without non-disturbing water-miscible co-solvents, temperatures within 0–40° C. and pH-values within 4–10.

The anti-HNL antibody used may be prepared by standard techniques well-known for other antibodies. The term encompasses polyclonal as well as monoclonal antibodies and antibodies produced by recombinant techniques. The term anti-HNL antibody means an antibody preparation reacting specifically with HNL, such as in monomeric forms, HNL as included in di-, multi or heteromeric forms and/or fragments of monomeric HNL exhibiting HNL unique determinants and epitopes. An anti-HNL antibody to be used in the inventive diagnostic method has no substantial reaction with other components that may be present in the sample or assay medium, particularly not with other neutrophil proteins, such as myeloperoxidase, cathepsin G, lactoferrin, lysozyme and elastase, or eosinophil proteins, such as eosinophil cationic protein (ECP), eosinophil protein X (EPX). By the term "substantially no reaction" is meant that the antibody has no disturbing reactivities for the intended purpose (for instance assay). See further the experimental section. Unless otherwise specified, the antibody concept above, in particular the anti-HNL antibody concept, also comprises antibody active fragments and derivatives, including Fab, F(ab)$_2$, Fv, single chain antibody etc and any other biospecific affinity reactant bindning specifically to HNL.

Rabbit anti-HNL antibodies are novel except for polyclonal variants (J. Biol. Chem. 268 (1993) 10425–10432). In view of the unexpected advantage of using anti-HNL antibodies in differentiating bacterial from viral infections, all anti-HNL antibodies except the polyclonal rabbit variants are claimed patentable and form one aspect of the invention. Thus this aspect of the invention comprises mammalian antibodies of mouse, rat, dog, human, cat, cow, sheep etc origin, and reptile and avian antibodies (for instance of salamander, chicken or budgerigar origin). Common techniques for preparation of antibodies are applicable (polyclonal, monoclonal and recombinant methods).

The best mode developed at the priority date is given in the experimental section.

At the end of the priority year, the best mode protocol from a commercial point of view was believed to be the use of an anti-HNL antibody linked to a solid support for catching HNL from the sample and an enzyme labelled anti-HNL antibody to accomplish detection/quantitation of the HNL caught on the solid support. The preferred solid supports and enzyme substrates in this mode were believed to be porous cellulose matrices and fluorogenic substrates, respectively.

The invention is further defined in the appending claims and is illustrated in the experimental section.

EXPERIMENTAL SECTION

Isolation and Purification of Human Neutrophil Lipocalin (HNL)

Isolation of granules:

Granules were prepared from the buffy coat of granulocytes obtained from normal human blood. The buffy coats, approximately 3 L, were mixed in measuring cylinders with an equal volume of 2% Dextran T-500 in phosphate-buffered saline (Dulbecco, without calcium and magnesium). The red blood cells were allowed to sediment for approximately 1 h at room temperature before collecting the granulocyte-rich plasma. The granulocytes were washed twice in the buffer and once in 0.34 M sucrose by centrifugation at 400× g for 10 minutes and then homogenized in a Potter-Elvehjem homogenizer. Homogenization was checked by phase-contrast microscopy and was stopped when approximately 90% of the granulocytes had been broken. The homogenate was then mixed with an equal volume of 0.34 M sucrose, 0.3 M NaCl, and centrifuged for 20 minutes at 450× g at 4° C. to eliminate whole cells, cell membranes and nuclei. The supernatant was centrifuged for 20 minutes at 10,000× g to sediment the granules. After one cycle of freezing and thawing, the granule pellet was extracted with 5 volumes of 0.05 M acetic acid, pH 4.5, for 1 h at 4° C. An equal volme of 0.4 M sodium acetate, pH 4.0, was then added, and the extraction procedure was continued by magnetic stirring for 3 h at 4° C. The granule extract was centrifuged for 30 minutes at 12,000× g, and the supernatant containing the granule proteins was collected and concentrated using a YM-10 (Amicon, U.S.A.) filter to approximately 5 ml for further purification.

Chromatographic procedures:

The concentrated granule proteins were subjected to gel filtration chromatograhpy on Sephadex® G-75 column (Pharmacia Biotech AB, Uppsala, Sweden), see FIG. 1. The peaks of proteins of the chromatogram were pooled as indicated in the figure (pools 1, 2, 3 and 4) and concentrated by using a YM-10 filter. Each of the pools as well as the granule extract was subjected to analytical agarose electrophoresis on purified agarose as described earlier (Olsson et al., Blood 44 (1974) 235-; and Johansson, J. Clin. Lab. Invest. 29 Suppl. (1974) 124-). The proteins from the third and fourth pool were subjected to ion-exchange chromatography by means of FPLC® (Pharmacia Biotech AB, Sweden) using a strong cationic exchanger Mono-S in a prepacked column with proteins appearing in three peaks (A, B and C). See FIG. 2. Finally the middle peak (B) was subjected to gel filtration chromatography on a Superose® 12 HR column by means of FPLC® with only one single peak appearing in the chromatogram (FIG. 3).

Analysis by SDS-PAGE:

Sodium dodecyl sulphate polyacrylamide electrophoresis (SDS-PAGE) was performed according to Laemmli (Nature 220 (1970) 680-) on 15% polyacrylamide. Both unreduced and reduced samples (treatment with 12 mM dithiotreitol at 95° C. for 7 minutes) were subjected to electrophoresis. Unreduced samples were treated under the same conditions as reduced samples except for the omission of dithiotreitol. Proteins were visualized by silver staining. The silver stained gels illustrated that the protein was purified to apparent homogeneity and had a molecular weight of about 45 kD in the unreduced state and 24 kD in the reduced state. This data indicated that the protein was made up two apparently identical chains (subunits), which also was in agreement with data obtained on chromatofocusing and isoelectric focusing.

Miscellaneous:

The proteinase inhibitors phenylmethylsulfonyl fluoride (PMSF) (100 μg/ml) and soybean trypsin inhibitor (SBTI) (100 μg/ml), were added to all buffers from the homogenization step to the first ion-exchange chromatography.

The isoelectric point of the isolated HNL was about pH 8.40 (not shown) as determined by isoelectric focusing on Ampholine® PAGplate (pH 3.5–9.5) on a Multiphor® II unit (Pharmacia Biotech AB, Sweden) with coomassie blue staining.

Preparation of Neutrophil Granule Release Products and Post-nuclear Supernatant:

Human neutrophils were isolated from buffy coats as described above. Remaining erythrocytes were removed by hypotonic lysis. Briefly, 18 ml water was added to 6 ml cell suspension for 30 sec. Tonicity was restored with 6 ml of 3.6% NaCl. The cells were equilibrated at 37° C. at $10^7$–$10^8$ cells/ml in Dulbecco's phosphate buffered saline. After equilibration, the cells were stimulated to degranulate by treating with 1 µg/ml of phorbol myristate acetate (PMA) for 5 min and pelleted by centrifugation. The resulting supernatant was collected. The post-nuclear supernatant was prepared from disrupted human neutrophils as described above.

Amino Acid Analysis:

Automated amino acid sequence analysis (Wilhelm et al., J. Biol. Chem. 264 (1989) 17213-) was performed with an ABI 477A amino acid sequencer equipped with an on-line PTH analyser (Applied Biosystems, U.S.A.). The 10 protein was treated with trypsin and the digest separated by reversed phase chromatography on a 2.1 mm×30 mm RP18 column and eluted with a gradient of acetonitril in water, both solvents contained 0.1% trifluoroacetic acid. Collected fractions were analysed by plasma desorption mass spectrometry (PDMS, Edman P et al., Eur. J. Biochem. 1 (1967) 80-) on a BioIon mass spectrometer (Applied Biosystems). The mass spectra were used for choosing fractions for further sequence analysis and as a control for the determined sequences.

The protein data bases Pir-Protein (release 9/91) and SwissProt (release 5/92) were searched by use of the algoritm FASTA (Sundqvist et al., Mass Spectrom. Rev. 4 (1985) 421-) utilising the UWGCG software (Pearson et al., Proc. Natl. Acad. Sci. USA 85 (1988) 2444-).

The N-terminal amino acid sequence and four tryptic fragments including 62 amino acids of HNL were analysed. The result indicated a sequence identity with human neutrophil 24 kD N-formyl-peptide binding protein, 25 kD alpha-2-microglobulin-related protein (Triebel et al., FEBS Lett. 314 (1992) 386-) and neutrophil gelatinase-associated lipocalin (NGAL) (Kjeldsen et al., J. Biol. Chem. 268 (1993) 10425-). The latter two proteins were recently identified by two other groups who showed that the protein was covalently associated with gelatinase forming 125 or 135 kD heterodimeric complex (Triebel et al., FEBS Lett. 314 (1992) 386-; and Kjeldsen et al., J. Biol. Chem 268 (1993) 10425-). We consider that a 140 kD band detected by our immunoblotting of the non-reduced post-nuclear supernatant represents the heterodimer of HNL with gelatinase. Human neutrophil 24 kD N-formyl-peptide binding protein, 25 kD alpha-2-microglobulin-related protein, neutrophil gelatinase-associated lipocalin and our HNL are likely identical proteins.

Immunochemical Properties of HNL:

Double immunodiffusion (Devereux et al., Nucleic Acid research 12 (1984) 387-) showed that the protein did not react with polyclonal antibodies against other neutrophil proteins (cathepsin G, elastase, myeloperoxidase, lysozyme and lactoferrin), eosinophil proteins (ECP, EPX/EDN and eosinophil peroxidase).

Production of Antibodies:

Polyclonal antibodies

Antibodies against HNL were raised in rabbits by multiple site intracutaneous injections into the rabbits of a total of 72 µg of the purified protein (from the column with Superose® 12 HR) homogenised in Freund's complete and incomplete adjuvant. The specificity of the antibodies was evaluated by double immunodiffusion (Devereux et al., Nucleic Acid research 12 (1984) 387-) in agarose and tested against extracts of neutrophil granules and the following purified proteins: cathepsin G, elastase, myeloperoxidase, lysozyme, lactoferrin, eosinophil cationic protein (ECP) and eosinophil protein X (EPX/EDN). The antibodies reacted only with HNL.

Monoclonal antibodies:

Immunization: Female Balb/c mice, age 2–3 months, were immunized subcutaneously with HNL. Priming was done by injecting 50 µg impure HNL mixed with Freund's complete adjuvant. Three boosters were done 50, 50 and 32 µg of pure or impure HNL (different mice) in PBS (phosphate buffered saline). These were administered 4, 8 and 18 weeks after the priming. Three prefusion boosters were given on consecutive days prior to the fusions. Fusions were performed 19–30 weeks after the first immunization with spleen cells from three mice, while the spleen from the fourth mouse was frozen for future use.

Fusions: Fusions were done principally as described by Galfré et al. (Nature 266 (1977) 550–552). Lymphocytes from the spleens were separated from erythrocytes on a density gradient (Percoll®, Pharmacia Biotech AB, see booklet "Percoll®: Methodology and Applications" and "Instructions for use"). Thereafter fusions were done with Sp2/0 myeloma cells. Polyethylene Glycol (PEG) 1500 (art no 29575, BDH Limited, Poole, England) was used as fusing agent. The fused cells were seeded at a myeloma cell concentration of $0.2$–$0.8 \times 10^5$/well.

Screening: Culture supernatants were tested with ELISA technique using 1 µg antigen coated to the wells. Screening against impure HNL revealed after the three fusions respectively 101/2/109 positive hybridomas. The mouse yielding only 2 positive clones had been boosted with pure HNL (apart from the first immunization) while the other two mice were boosted with impure HNL. Antibodies which were found to be reactive against impure HNL were also tested with pure HNL. This further screening revealed 18/0/9 positive hybridomas. Of the 27 hybridomas 23 were of IgG1 subclass and therefore of interest. All HNL positive clones were tested for cross-reactivity with MPO and all but one were found negative.

Studies with BIAcore®: The supernatants from these 23 hybridomas were screened for specificity to both impure and pure HNL in BIAcore® (Pharmacia Biosensor AB, Uppsala, Sweden). Also a partial epitope mapping was done in BIAcore®.

Testing in assays: After considering the specificity against pure HNL, the epitope mapping and dilution curves in ELISA with pure HNL, four hybridomas were cloned, expanded and purified before tested in an HNL Pharmacia RIA with $^{125}$I-HNL labelled pure HNL (Competitive assay: a mixture of $^{125}$I-HNL and HNL is reacted with a functionally deficient amount of anti-HNL antibody in an aqueous liquid phase followed by precipitation with an anti-mouse antibody bound to agarose particles, separation and measurement of $^{125}$I-HNL bound to the agarose particles). Two of the monoclonals selected ($mab_1$ and $mab_2$) were found to perform well in an assay comprising the steps: (a) incubation of sample HNL with a porous integral matrix carrying a first anti-HNL monoclonal ($mab_1$), (b) separation, (c) incubation of matrix with a second anti-HNL monoclonal ($mab_2$; labelled and different from the matrix-bound monoclonal) in a prototype Pharmacia CAP RIA for HNL (Pharmacia Diagnostics AB, Sweden).

IMMUNOBLOTTING:

For immunoblotting the proteins were transferred from SDS-PAGE in a 8–25 gradient gel to 0.2 µm nitrocellulose filter (Bio-Rad Laboratories, Richmond, Calif., USA) on Phast® system (Pharmacia Biotech AB, Sweden). Additional binding sites were blocked by incubating the nitrocellulose filter in 3% gelatine in 20 mM Tris buffer including 0.5 M NaCl, pH 7.5, for 2 h. After three washes in Tris buffer, 0.1% Tween®, the blot was incubated with the primary antibodies (directed against HNL) diluted 1:1000 in Tris buffer, 1% gelatine, 0.1% Tween® for 2 h. The primary antibodies adhering to the gel were labelled with peroxidase-conjugated swine anti-rabbit antibody (Sigma) diluted in Tris buffer, 1% gelatine, 0.1% Tween® and incubated for 1 h. The filter was then washed 3 times in Tris buffer, 0.1% Tween®, and developed in 50 ml of 0.06 M sodium tetraborate buffer pH 9.7 containing 60 mg $MgSO_4$, 25 mg beta-naphthyl phosphate (Sigma) and 25 mg o-dianisidine tetrazotized (Sigma).

The immunoblotting procedure was applied to testing of the specificity of the antibodies by reaction with release products and post-nuclear supernatant from neutrophils. With the non-reduced post-nuclear supernatant several bands were detected at approximate molecular weights of 140–240 kD, 43–45 kD and 24 kD. After reduction only one band at the molecular weight of 24 kD was seen. With the non-reduced released material three bands were found with apparent molecular weights of >200 kD, 45 kD and 24 kD. After reduction of the released material only one band at an apparent molecular weight of 24 kD was seen. These findings indicated that the antibodies specifically identified the protein, but that the protein existed in the cell and after extracellular release in multiple forms.

Radioimmunoassay

A. Procedure (double antibody radioimmunoassay).

HNL was labelled with $^{125}$I (Amersham, U.K.) by the chloramine-T method (Hunter et al., Nature 194 (1962) 495-). Free $^{125}$I was separated from labelled protein by gel filtration on a Sephadex G-75 column, and labelled protein was stored at 4° C. The specific activity of the labelled protein was 2.29 MBq/µg HNL. Protein standard (4–256 µg/L) was prepared from purified protein, diluted in assay buffer (see below) and stored at −70° C. until used;

they were not re-frozen. A 50 µl solution of either sample or standard was sequentially mixed with 50 µl of labelled HNL (diluted to 8 µg/L in dilution buffer), 50 µl of anti-HNL antibodies diluted 1:3,800 in assay buffer ((0.05 M sodium phosphate, pH 7.4, containing 0.08 M NaCl, 0.01 M Na-EDTA, 0.2% (w/v) bovine serum albumin, 0.02 (w/v) $NaN_3$, 0.2% (w/v) CTAB (N-cetyl-N,N,N-trimethylammonium bromide) and 0.5% (v/v) Tween® 20 (KEBO AB, Sweden))) and incubated for 3 h at room temperature. Thereafter, 2 ml of decanting suspension containing anti-rabbit IgG raised in sheep and covalently linked to Sepharose® (Pharmacia Diagnostics AB, Sweden) was added and the incubation continued for 30 minutes at room temperature. Complexes between HNL/HNL-$^{125}$I and the anti-HNL antibody became bound to Sepharose and could subsequently be separated and pelleted by means of centrifugation at 18° C. for 10 minutes at 3,000 rpm. After decantation, the radioactivity was measured 1 minute/tube in a gamma counter.

B. Blood samples:

Serum samples were prepared by allowing blood to clot at room temperature for 60 min, followed by centrifugation twice at 1350× g for 10 minutes. EDTA-containing plasma were prepared by pelleting blood cells by means of centrifugation twice at 1350× g for 10 minutes.

C. Statistical evaluation:

Man-Whitney U test, Student's test and regression analysis were used. All statistical calculations were preformed on a personal computer by means of the statistical package Statistica (Statsoft, USA).

D. Specificity and range of measurement:

Cross reactivity with lysozyme (3.7–900 µg/L), lactoferrin (1.9–426 µg/L), myeloperoxidase (8–1000 µg/L), elastase (2.9–750 µg/L), ECP (2–200 µg/L) and EPX (3–400 µg/L) were tested in the assay and found to be undetectable, indicating high specificity of both the antibody and the assay. The range of measurement was 4–256 µg/L and the detection limit was less than 4 µg/L. Serum was diluted serially to test for parallelism between the standard curve and the curve obtained for the dilutions. The parallelism was almost complete.

E. Recovery and reproducibility:

An average recovery of 102.5% (range 100.40–106.66%) was obtained when purified HNL of four different concentrations (4–32 µg/L) was added to normal serum. The intra and inter assay coefficients of variation were less than 6% (n=10) and 10% (n=10), respectively.

F. Normal levels of HNL in the circulation:

The normal levels of HNL in serum and plasma were 78.40±23.70 µg/L (±SD) (range 37.95–190.87 µg/L) and 50.65±11.43 µg/L (±SD) (range 30.51–105.80 µ/L), respectively. There were no sex and age differences, and the levels in serum were significantly higher than in plasma (p<0.001) but well correlated (r=0.684, p<0.001).

G. Patient study:

The patient group consisted of 61 patients, 31 women and 30 men, aged from 7 to 86, mean age 47, with clinically diagnosed acute bacterial or viral infections. In the group of 34 patients with bacterial infections 16 had pneumonia, 1 pleuritis, 10 acute upper urinary tract infections, 5 bacterial enteritis, 3 tonsillitis, 2 soft skin infection and 2 septicaecima. The blood samples at day 0 were drawn before initiation of antibiotic therapy and thereafter each day in consecutive days. In the 26 patients with acute viral infections 5 had influenza A, 1 influenza B, 3 measles, 5 viral meningitis, 4 common cold, 3 acute mononucleosis, 1 varicellae, 1 RSV-infection and 1 viral gastroenteritis. The blood samples were drawn within one to 24 h after the admittance to the hospital (both in and outward patients). All patients in the study had fever more than 38° C. at the admittance and no patient had immunosuppressive treatment or disease. Patients who had both a verified bacterial and viral infection were excluded, as those in which no conclusive clinical or laboratory diagnosis could be established. Patients with two positive bacterial cultures were included.

The bacterial diagnoses were established by clinical examination and/or positive cultures in blood, liquor, and stool, throat, biopsy and wound.

The viral diagnoses were confirmed by serology (fourfold antibody rise, or IgM positive), viral isolation, or by immunofluorescence detection of virus antigen, or clinical signs, history and negative cultures for pathogen bacteria.

Analysis of C-reactive protein (CRP) was performed by immunonephelometry at the routine department of clinical chemistry.

H. Result of the patient study:

Sera and plasma from patients acutely infected by bacteria or viruses were measured for HNL. The concentrations of HNL in sera and plasma of patients infected by viruses and bacteria (before the treatment) were 93.78±45.30 µg/L (±SD) and 404.14±355.02 µg/L (±SD) in serum and 47.81±18.18 µg/L (±SD) and 145.46±194.32 µg/L (±SD) in plasma, respectively. Elevated levels were found in sera and plasma of patients infected by bacteria, but not by viruses. The concentrations of CRP in sera of patients infected by viruses and bacteria were 36.5±32.6 mg/L (±SD) and 155.0±123.4 mg/L (±SD), respectively, and there was a significant difference, p<0.001. The level of HNL in sera was significantly correlated to that in plasma. Four patients were followed for three days for clinical investigation during treatment. Their levels were gradually decreased.

The sensitivity, specificity and predictive value of positive and negative test of the individual determinations of CRP and HNL are given in the Table.

The optimal cut-off level for CRP seemed to be at 50 mg/L. At this level the predictive values are about 80%. For HNL the optimal level was 155 µg/L with a positive predictive value of 98% and a negative predictive value of 89%.

Discussion of the result

The significantly elevated levels found in sera and plasma of patients infected by bacteria illustrate the value of HNL level as an early indicator of bacterial infections.

After therapy with the appropriate antibiotics, HNL levels decreased. The kinetic investigation demonstrates that the determination of HNL may be useful in monitoring the effects of the treatment. The HNL levels in sera and plasma did not increase during viral infections. Therefore, the HNL level might be useful in the distinction between viral and bacterial infections. To differentiate between patients with viral and bacterial infections, three cut-off values of 190 µg/L, 155 µg/L and 100 µg/L were tested for HNL. The cut-off value of 190 µg/L, which is the upper limit of normal serum HNL level gave the highest sensitivity but lowest specificity, and 100 µg/L, the mean normal serum level plus one SD, gave the lowest sensitivity and a high specificity. When setting the cut-off value of 155 µg/L, the mean normal serum level plus about three SDs, the sensitivity of 92% and specificity of 96% were obtained. The normal serum HNL levels range from 37.95 to 190.87 µg/L (mean =78.40±23.70 µg/L, n=100). Except in one subject, all levels of HNL in normal sera were below 155.00 µg/L. Of 34 serum samples in bacterial infections, 33 serum HNL levels were above 155.00 µg/L, with one exception (this patient, who had a level of 43.00 µg/L which was much lower than the normal mean serum HNL level, was diagnosed as pleuritis). The explanation for this might be a partial HNL-deficiency of the neutrophil granules. Among 26 serum samples of patients with viral infections, three serum HNL levels were above 155.00 µg/L. One of these patients with measles might have been superinfected with a bacterial infection, since white blood cells (WBC) and CRP were also highly elevated.

As compared to CRP the measurement of HNL in serum was superior in the distinction between bacterial and viral infections. Thus in order to obtain a sensitivity with CRP that approached HNL, the cut-off had to be 100 mg/L. At this level, however, the specificity was clearly unacceptable.

In preliminary experiments we have found subnormal HNL levels in individuals suffering from hepatic diseases and in bone marrow transplanted patients. In the latter case the HNL-level reached normal levels if the transplant was accepted.

Table:

Sensitivity, specificity and predictive value of a positive and a negative test for CRP and HNL in the discrimination between acute viral and bacterial infections.

| Determination | Cut-off value | Sen. | Spec. | Predic. P | Predic. N* |
|---|---|---|---|---|---|
| CRP (mg/L) | >100 | 92 | 67 | 63 | 94 |
| | >50 | 84 | 78 | 82 | 81 |
| | >20 | 60 | 82 | 95 | 27 |
| | >10 | 59 | 100 | 100 | 16 |
| HNL (µg/L) | >190 | 97 | 81 | 82 | 96 |
| | >155 | 92 | 96 | 98 | 89 |
| | >100 | 79 | 95 | 97 | 67 |

*Sen = Sensitivity; Spec = Sepcificity; Predic P = Prediditive value of a positive test; Predic N = Predicitive value of a negative test.

LEGENDS TO THE FIGURES

FIG. 1. Gel filtration chromatography on Sephadex G-75 of granule extracts obtained from healthty blood donors.

The column (2.5×90 cm) was equilibrated with 0.2 M NaAc pH 4.5. The sample volume was 5 ml and fractions of 2.5 ml were collected at a flow rate of 5 ml/h. Protein was determined by its absorbance at 280 nm.

Results from a radioimmunoassay of HNL is included in the chromatogram (fractions 60–90). Protein in the peaks was pooled as indicated at the bottom of the chromatogram (pools 1, 2, 3 and 4). The upper right insert shows the electrophoretic pattern of a granule extract (E) and pools 1–4 from the gel filtration. Electrophoresis was run at pH 8.6 in purified agarose. The cathode is on top. The broken horizontal line indicates the starting positions.

FIG. 2. Ion exchange chromatography on Mono-S prepacked column of the protein containing pool from Sephadex G-75 gel filtration.

The Mono-S column was equilibrated with 0.1 M NaAc pH 5.67. The sample buffer was changed on a PD-10 column with 0.1 M NaAc pH 5.67. The sample was applied on the Mono-S column and eluted by a linear gradient from 0.1 to 0.5 NaAc pH 5.67. Fractions were collected at a flow rate of 0.5 ml/min. HNL was located to peak B that was rechromatographed on the same column.

FIG. 3. Gel filtration chromatography of the peak containing HNL from re-ion exchange chromatography on Superose 12 HR column.

The protein was eluted with 0.1 M NaAc, 0.15 M NaCl, pH 5.67. Fractions were collected at a flow rate of 0–0.5 ml/min. The protein was eluted a pure protein in one peak.

What is claimed is:

1. A method of diagnosing human disease, comprising measuring a level of human neutrophil lipocalin (HNL) in a sample from an individual human to be diagnosed, wherein a measured value which is higher than the normal level is an indication that the individual suffers from an inflammation.

2. A method according to claim 1, wherein the human disease is inflammation caused by a bacterial infection.

3. A method according to claim 1, wherein a measured value which is higher than the normal level is an indication that the individual suffers from an inflammation that with a greater than 80% likelihood is caused by a bacterial infection.

4. A method according to claim 1, wherein the sample is a blood sample.

5. A method according to claim 1, wherein the sample is a plasma sample, a serum sample or broncho alveolar lavage.

6. A method according to claim 1, wherein the HNL is measured by an immunoassay.

7. A method according to claim 1, wherein the level of HNL is measured by contacting the sample with anti-HNL antibody linked to a solid support to catch the HNL and then contacting the caught HNL with an enzyme-labeled anti-HNL antibody.

8. A method according to claim 7, wherein the solid support comprises porous cellulose matrix and the enzyme is provided with a fluorgenic substrate.

* * * * *